US00PP19718P2

(12) United States Plant Patent
Jepsen

(10) Patent No.: US PP19,718 P2
(45) Date of Patent: Feb. 17, 2009

(54) ***KALANCHOE* PLANT NAMED 'MEGAN'**

(50) Latin Name: *Kalanchoe blossfeldiana*
Varietal Denomination: Megan

(75) Inventor: Knud Jepsen, Hinnerup (DK)

(73) Assignee: Knud Jepsen A/S, Hinnerup (DK)

( * ) Notice: Subject to any disclaimer, the term of this patent is extended or adjusted under 35 U.S.C. 154(b) by 0 days.

(21) Appl. No.: 12/079,328

(22) Filed: Mar. 25, 2008

(51) Int. Cl.
*A01H 5/00* (2006.01)

(52) U.S. Cl. ..... Plt./341

(58) Field of Classification Search ..... Plt./341
See application file for complete search history.

*Primary Examiner*—Annette H Para
(74) *Attorney, Agent, or Firm*—C. A. Whealy

(57) ABSTRACT

A new and distinct cultivar of *Kalanchoe* plant named 'Megan', characterized by its medium in size, upright, uniform and moderately vigorous growth habit; medium-sized dark green-colored leaves; uniform and freely flowering habit; medium-sized double red-colored flowers; and excellent postproduction longevity.

2 Drawing Sheets

Botanical designation: *Kalanchoe blossfeldiana.*
Cultivar denomination: 'Megan'.

BACKGROUND OF THE INVENTION

The present invention relates to a new and distinct cultivar of *Kalanchoe,* botanically known as *Kalanchoe blossfeldiana,* and hereinafter referred to by the name 'Megan'.

The new *Kalanchoe* is a product of a planned breeding program conducted by the Inventor in Hinnerup, Denmark. The objective of the breeding program is to create new double-flowered *Kalanchoe* cultivars with attractive foliage and flower coloration.

The new *Kalanchoe,* originated from a cross-pollination made by the Inventor in Hinnerup, Denmark in April, 2005, of the *Kalanchoe blossfeldiana* cultivar KJ 2003 1487, not patented, as the female, or seed parent with the *Kalanchoe blossfeldiana* cultivar Juliana 2000, not patented, as the male, or pollen, parent. The cultivar Megan was discovered and selected by the Inventor as a flowering plant from within the progeny of the stated cross-pollination in a controlled environment in Hinnerup, Denmark in November, 2005.

Asexual reproduction of the new *Kalanchoe* by vegetative terminal cuttings in a controlled environment in Hinnerup, Denmark since March, 2006, has shown that the unique features of this new *Kalanchoe* are stable and reproduced true to type in successive generations.

SUMMARY OF THE INVENTION

The cultivar Megan has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Megan'. These characteristics in combination distinguish 'Megan' as a new and distinct cultivar of *Kalanchoe:*

1. Medium in size, upright, uniform and moderately vigorous growth habit.
2. Medium-sized dark green-colored leaves.
3. Uniform and freely flowering habit.
4. Medium-sized double red-colored flowers.
5. Excellent postproduction longevity.

Plants of the new *Kalanchoe* can be compared to plants of the female parent, the cultivar KJ 2003 1487. Plants of the new *Kalanchoe* differ from plants of the cultivar KJ 2003 1487 primarily in petal quantity as plants of the new *Kalanchoe* have flowers with more petals than plants of the cultivar KJ 2003 1487.

Plants of the new *Kalanchoe* can also be compared to plants of the male parent, the cultivar Juliana 2000. Plants of the new *Kalanchoe* differ from plants of the cultivar Juliana 2000 in the following characteristics:

1. Plants of the new *Kalanchoe* and the cultivar Juliana 2000 differ in leaf shape as leaves of plants of the cultivar Juliana 2000 have more cordate-shaped bases.
2. Plants of the new *Kalanchoe* have double flowers whereas plants of the cultivar Juliana 2000 have single flowers.

Plants of the new *Kalanchoe* can be compared to plants of the *Kalanchoe blossfeldiana* cultivar Cate, not patented. In side-by-side comparisons conducted in Hinnerup, Denmark, plants of the new *Kalanchoe* differed from plants of the cultivar Cate in the following characteristics:

1. Plants of the new *Kalanchoe* were more compact than plants of the cultivar Cate.
2. Plants of the new *Kalanchoe* and the cultivar Cate differed in leaf shape as leaves of plants of the cultivar Cate had more cordate-shaped bases.
3. Flowers of plants of the new *Kalanchoe* had fewer petals than flowers of plants of the cultivar Cate.

BRIEF DESCRIPTION OF THE PHOTOGRAPHS

The accompanying colored photographs illustrate the overall appearance of the new *Kalanchoe,* showing the colors as true as it is reasonably possible to obtain in colored reproductions of this type. Colors in the photographs may differ slightly from the color values cited in the detailed botanical description which accurately describe the colors of the new *Kalanchoe*.

The photograph on the first sheet comprises a side perspective view of a typical flowering plant of 'Megan' grown in a container.

The photograph on the second sheet comprises close-up views of typical vegetative (top left) and generative (top right) leaves, upper (center left) and side (center right) perspective views of typical flowers and a side perspective view of a typical flowering stem (bottom) of 'Megan'.

DETAILED BOTANICAL DESCRIPTION

The aforementioned photographs and following observations, measurements and values describe plants grown in Hinnerup, Denmark in a glass-covered greenhouse during the winter and under conditions which closely approximate commercial production. During the production of the plants, day temperatures were about 19° C., night temperatures were about 21° C. and light levels ranged from 10 kilolux to 50 kilolux. Unrooted cuttings were directly stuck in containers and received long day/short night conditions (more than 14 hours of light) for about two weeks; plants then received photoinductive short day/long night conditions (minimum 14 hours darkness) until flowering. Plants were about eleven weeks old when the photographs and the description were taken. In the detailed description, color references are made to The Royal Horticultural Society Colour Chart, 2001 Edition, except where general terms of ordinary dictionary significance are used.

Botanical classification: *Kalanchoe blossfeldiana* cultivar Megan.

Parentage:

*Female, or seed, parent.*—*Kalanchoe blossfeldiana* cultivar KJ 2003 1487, not patented.

*Male or pollen parent.*—*Kalanchoe blossfeldiana* cultivar Juliana 2000, not patented.

Propagation:

*Type.*—By vegetative terminal cuttings.

*Time to initiate roots, summer.*—About two weeks at temperatures of 19° C. to 21° C.

*Time to initiate roots, winter.*—About 19 to 21 days at temperatures of 19° C. to 21° C.

*Time to produce a rooted young plant, summer.*—About three weeks at temperatures of 19° C. to 21° C.

*Time to produce a rooted young plant, winter.*—About 24 days at temperatures of 19° C. to 21° C.

*Root description.*—Fine, fibrous; white in color.

*Rooting habit.*—Freely branching; moderately dense.

Plant description:

*Plant habit.*—Upright, uniform and moderately vigorous growth habit. Very freely flowering with numerous compound cymes. Inverted triangle with rounded crown. Appropriate for 6-cm to 13-cm containers.

*Plant height at flowering.*—About 18 cm.

*Plant diameter at flowering.*—About 25 cm.

*Branching habit.*—Usually about three to five lateral branches develop per plant. Pinching (removal of the terminal apex) is not required but will enhance lateral branch development.

Lateral branch description:

*Length.*—About 8 cm to 12 cm.

*Diameter.*—About 4 mm.

*Internode length.*—About 1 cm to 1.5 cm.

*Aspect.*—Erect.

*Strength.*—Strong.

*Texture.*—Smooth, glabrous.

*Color.*—Close to 146A.

Foliage description:

*Arrangement.*—Opposite, simple; generally symmetrical.

*Length, vegetative plants.*—About 8 cm to 13 cm.

*Width, vegetative plants.*—About 6 cm to 10 cm.

*Length, generative plants.*—About 5 cm to 13 cm.

*Width, generative plants.*—About 2 cm to 10 cm.

*Shape.*—Ovate.

*Apex.*—Rounded.

*Base.*—Cordate to sagittate.

*Margin.*—Crenate.

*Texture, upper and lower surfaces.*—Glabrous, leathery; succulent.

*Venation pattern.*—Pinnate.

*Color.*—Developing and fully expanded foliage, upper surface: Close to 147A; venation, close to 147A. Developing and fully expanded foliage, lower surface: Close to 147B; venation, close to 147B.

*Petiole.*—Length: About 0.2 cm to 2.5 cm. Diameter: About 5 mm to 11 mm. Texture, upper and lower surfaces: Smooth, glabrous. Color, upper surface: Close to 147A. Color, lower surface: Close to 147B.

Flower description:

*Flower arrangement and habit.*—Double flowers arranged singly in compound dichasial cymes that arise from leaf axils. Uniform and freely flowering habit with usually about 30 to 50 flowers per inflorescence. Flowers not persistent. Flowers not fragrant.

*Natural flowering season.*—Plants of the new *Kalanchoe* initiate and develop flowers under short day/long night conditions or during the late autumn/winter/early spring. Flower initiation and development can also be induced under artificial short day/long conditions (at least 14 hours of darkness).

*Time to flower.*—Under short day/long night photoinductive conditions, about 75 days are required. Actual time to flower is primarily dependent upon temperature and light intensity.

*Post-production longevity.*—Excellent post-production longevity; plants maintain good foliage and flower substance for about six weeks under interior environmental conditions.

*Inflorescence height.*—About 5 cm to 10 cm.

*Inflorescence diameter.*—About 4 cm to 6 cm.

*Flower diameter.*—About 1.5 cm to 2.2 cm.

*Flower length (height).*—About 1 cm.

*Flower bud.*—Shape: Ovoid. Length: About 1.4 cm. Diameter: About 4 mm. Color: Close to 45B.

*Petals.*—Arrangement: About 15 fused at the base. Length (largest petals): About 1 cm. Width (largest petals): About 6 mm. Aspect: Slightly upright to eventually recurved. Shape: Ovate. Apex: Rounded. Margin: Entire. Texture, upper and lower surfaces: Smooth, glabrous. Color: When opening and fully opened, upper surface: Close to 45B. When opening and fully opened, lower surface: Close to 37A; dots, close to 45B.

*Sepals.*—Appearance: Four fused at the base. Length: About 7 mm. Width: About 2 mm. Shape: Lanceolate. Apex: Acute. Base: Truncate. Margin: Entire. Texture, upper and lower surfaces: Smooth; glabrous. Color, immature, upper and lower surfaces: Close to 146A. Color, mature, upper and lower surfaces: Close to 146A.

*Peduncles.*—Length: About 1 cm. Diameter: About 3 mm. Aspect: Erect to about 60° from vertical. Strength: Strong. Texture: Smooth, glabrous. Color: Close to 137C.

*Pedicels.*—Length: About 1 mm to 2 mm. Diameter: About 1 mm. Aspect: Erect to about 90° from vertical. Strength: Strong. Texture: Smooth, glabrous. Color: Close to 137C.

*Reproductive organs.*—Androecium: Stamen number: About five to ten per flower. Anther shape: Elliptic. Anther size: About 1 mm by 1 mm. Anther color: Close to 22A. Amount of pollen: Scarce. Pollen color: Close to 20A. Gynoecium: Pistil number: About four per flower. Pistil length: About 3 mm. Style length: About 2 mm. Style color: Close to 145A. Stigma shape: Round. Stigma color: Close to 145A. Ovary color: Close to 138A.

*Seed.*—Quantity per flower: About 50 to 60. Length: Less than 1 mm. Diameter: Less than 1 mm. Color, immature: Close to 145C. Color, mature: Close to 177A.

Temperature tolerance: Plants of the new *Kalanchoe* have been observed to tolerate temperatures from about 5° C. to about 30° C.

Pathogen/pest resistance: Plants of the new *Kalanchoe* have not been observed to be resistant to pests and pathogens common to *Kalanchoes*.

It is claimed:

1. A new and distinct *Kalanchoe* plant named 'Megan' as illustrated and described.

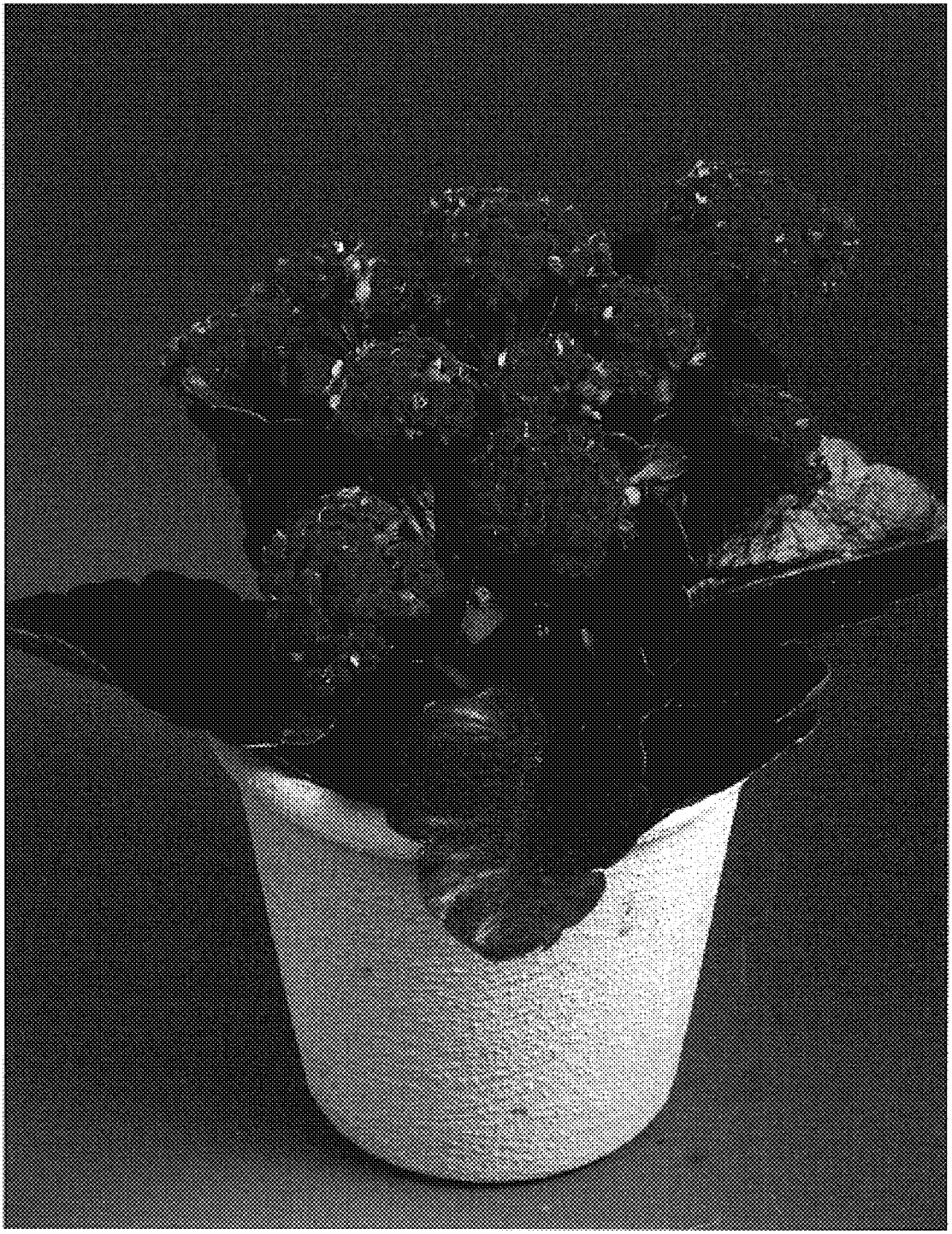

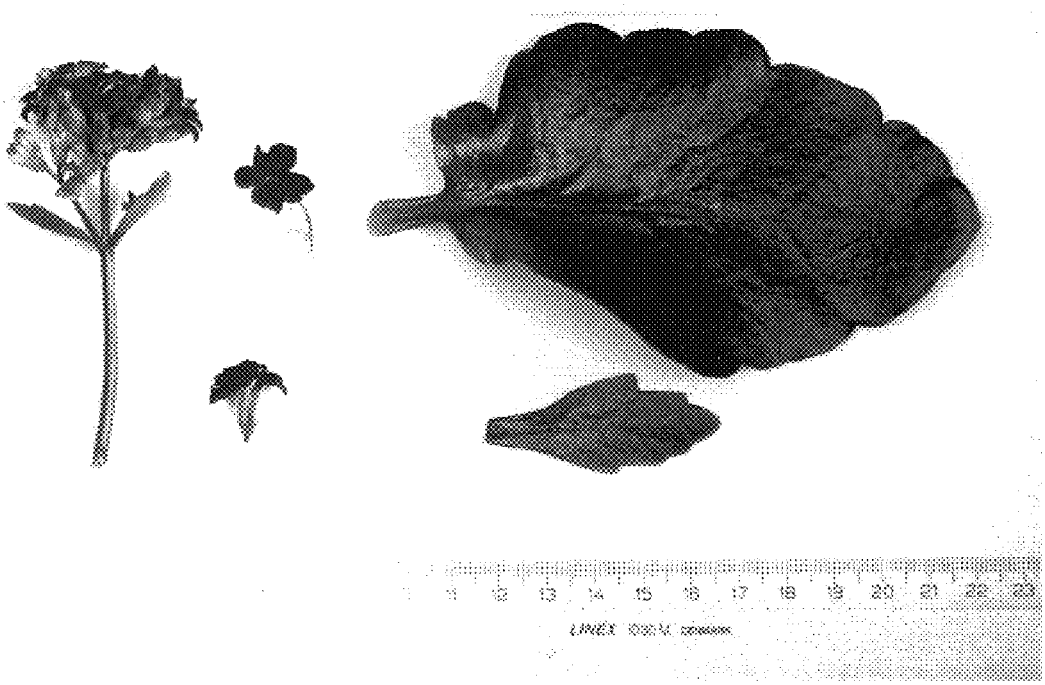

* * * * *